(12) United States Patent
Brady et al.

(10) Patent No.: US 8,124,050 B2
(45) Date of Patent: Feb. 28, 2012

(54) METHOD FOR COATING THE INTERNAL SURFACE OF A REACTION VESSEL

(75) Inventors: Frank Brady, London (GB); Nicholas Toby Jeffery, London (GB); Sajinder Kaur Luthra, London (GB); Erik Arstad, London (GB)

(73) Assignee: Hammersmith Imanet Limited, London (GB)

( * ) Notice: Subject to any disclaimer, the term of this patent is extended or adjusted under 35 U.S.C. 154(b) by 1302 days.

(21) Appl. No.: 10/583,647

(22) PCT Filed: Dec. 23, 2004

(86) PCT No.: PCT/GB2004/005410
§ 371 (c)(1), (2), (4) Date: Jun. 5, 2007

(87) PCT Pub. No.: WO2005/061110
PCT Pub. Date: Jul. 7, 2005

(65) Prior Publication Data
US 2007/0244324 A1    Oct. 18, 2007

(30) Foreign Application Priority Data
Dec. 23, 2003 (GB) .................................. 0329812.2

(51) Int. Cl.
*A61K 51/00* (2006.01)
(52) U.S. Cl. ....................................................... 424/1.11
(58) Field of Classification Search ......................... None
See application file for complete search history.

(56) References Cited

U.S. PATENT DOCUMENTS
5,262,031 A * 11/1993 Lux et al. ...................... 204/601
2004/0044100 A1 * 3/2004 Schlenoff et al. ............. 523/206

FOREIGN PATENT DOCUMENTS
WO         0073782        12/2000
WO    WO 0073782 A1  *  12/2000

OTHER PUBLICATIONS

Machine translation of WO 0073782 A1, Jan. 2010.*
Michael R. Buchmeiser: "Application of Metathesis in Heterogeneous Catalysis and Separation Sciences" Journal of Molecular Catalysis A: Chemical vol. 190, 2002, pp. 145-158.
Jurgen Falbe, Manfred Regits: "Rompp Chemie Lexikon" 1990, Georg Thieme Verlag, Stuttgart New York, p. 2026-2028.
Erik Arstad, et.al., "Rompgel-Supported Triphenylphosphine with Potential Application in Parallel Synthesis" Organic Letters, vol. 4, No. 11, 2002 pp. 1975-1977.
Michael Buchmeiser, et.al.,: Access to silica-and monolithic polymer supported C-C-coupling Catalysts via ROMP: applications in high-throughput screening reactor technology and biphasic catalysis Inorganica Chimica Acta, vol. 345, Mar. 2003, pp. 145-153.
Seeber, et.al., "Poly(7-Oxanorborn-2-ene-5,6-dicarboxylate)-coated Silica Prepared by Ring-Opening Metathesis Polymerization for the Selective Enrichment of Radioactive Lanthanides" Journal of Chromatography A. 848 (1999) pp. 193-202.
GB0329812.2 Search Report dated Jun. 2004.
PCT/GB2004/005410 Int'l Preliminary Report on Patentability dated Mar. 2006.
PCT/GB2004/005410 Int'l Search Report dated Apr. 2005.

* cited by examiner

*Primary Examiner* — Michael G Hartley
*Assistant Examiner* — Paul Dickinson

(57) ABSTRACT

A method for coating the internal surfaces of a reaction vessel having a small internal diameter comprises the steps of (i) introducing into the reaction vessel a solution of one or more monomers in a suitable solvent; (ii) introducing a flow of an inert gas through the reaction vessel; and (iii) initiating polymerization of the monomer solution.

18 Claims, 11 Drawing Sheets

(A)

(B)

(C)

METHOD FOR COATING THE INTERNAL SURFACE OF A REACTION VESSEL

This application is a filing under 35 U.S.C. 371 of international application No. PCT/GB2004/005410, filed Dec. 23, 2004, which claims priority to application No. 0329812.2 filed Dec. 23, 2003, in Great Britain the entire disclosure of which is hereby incorporated by reference.

The present invention relates to the field of solid phase chemistry, especially to reaction vessels for use in solid phase chemistry in which internal surface of the reaction vessel is coated with a polymer. The invention relates in particular to the coating with a polymer of solid phase reaction vessels having a small internal diameter, such as microfabricated tubes or loops, which are particularly suitable for radiochemistry. It is especially concerned with the coating of internal surface of such reaction vessels with a ring opening methathesis polymerisation (ROMP) polymer.

It is well known that many reactions are conveniently carried out on a solid phase and it is also known that the solid phase may comprise a coating on the internal surface of a reaction vessel.

Some reaction vessels, for example microfabricated devices, contain microchannels of small diameter and others, such as loops have a small internal diameter and it is therefore extremely difficult to provide a surface coating on such devices without blocking the channels of the device or omitting to coat some areas of the internal surface.

The present invention relates to a method of coating with a polymer the internal surface of microfabricated reaction vessels or reaction vessels with small internal diameter and to the coated devices.

Ring-opening metathesis polymerisation (ROMP) is a variant of the olefin metathesis reaction. One of the main advantages of ROMP polymers is that in principle every monomer unit carries a functional group and should give much higher loading than some other polymers. ROMP is known for the production of functionalised polymers for organic synthesis (Barrett et al Chemical Reviews 2002 102 pp 3301-24). A number of other chemical applications have been reported, e.g. chromatography, solid-phase extraction, construction of synthetic libraries and purification, all of which are discussed by Barrett et al.

The application of ROMP polymers to the surfaces of devices has also been reported. In WO 03/093406 ROMP polymers are suggested as a means to alter the surfaces of a miniaturised bioreactor to render them more biocompatible, i.e. that the cell viability and proliferation and/or other biological components produced by the cells are not adversely affected by contact with the surface.

In US 2002/0122747 microdevices are fabricated with ROMP polymers in order to enable metallization of the surfaces. The side chains of the ROMP polymer are selected such that they bind to the desired metal. The integration of components such as electrodes, heaters and valves is therefore permitted, rendering the microdevice more functional.

The present invention involves the application of polymers to the internal surfaces of a reaction vessel. The polymers can then act as a solid support for a solid phase physical or chemical process. The invention is especially concerned with reaction vessels coated with ROMP polymers and relates in particular to reaction vessels suitable for carrying out a solid-phase radiochemical process.

In a first aspect of the present invention there is provided a method of coating the internal surface of a device with a polymer, the process comprising the steps of:

(i) introducing into the device a solution of one or more monomers in a suitable solvent;
(ii) introducing a flow of an inert gas through the device; and
(iii) initiating polymerisation of the monomer solution.

The process is particularly suitable when the device is a microfabricated device or a reaction vessel with an internal diameter of less than about 2 mm.

The aim of step (ii) is to ensure that a coating of the polymer adheres to the internal surfaces whilst ensuring that the bore of the microchannels or the device itself remains unblocked. Step (ii) may take place either before or concurrently with step (iii).

Any suitable inert gas may be used, for example nitrogen or argon. However, nitrogen is particularly suitable.

The "internal surface" of the device is taken to mean the surface that comes into contact with the reactants introduced into the device. Therefore, when the internal surface is coated with a polymer, the reactants come into contact with the side chains of the polymer. The side chains themselves participate in the chemical process, and because they can be virtually any organic substituent the polymer can be tailored to be suitable for carrying out a specific chemical process.

In the context of the present specification a "microfabricated device" is a device in which predetermined networks of microchannels or capillaries, typically 10-300 µm, more typically 50-300 µm in diameter, are etched or otherwise machined on the surface of a substrate, suitably made of glass or silicon. Alternatively, the microchannels may be created using polydimethylsiloxane, which may be poured over a master (usually glass), allowed to cure and then peeled off, or are fabricated by injection moulding, hot embossing, casting, lithography, or machining. These channels may be sealed through bonding of a cover plate, suitably made from a metal (for example, gold, platinum or silver) or, more commonly, glass, to create a contained network capable of manipulating picolitre to microlitre volumes of liquid or gas. The sealing method used depends on the materials selected and may be selected from thermal bonding (for glass chips), anodic bonding (for silicon chips), and for polymer chips the sealing method may be selected from clamping, gluing, application of heat and pressure, and natural adhesion. Nanolitre and picolitre volumes may be used for analytical aspects but the devices can handle flows of up to hundreds of microlitres per minute. This could be increased further, for example, by stacking multiple devices. These devices are designed to be used either with micro syringe pumps (available from Kloehen Limited, Las Vegas, USA) or under electroosmotic flow. Fused silica capillaries can be used for interfacing with reagents or reagent sources and analytical systems (such as ultraviolet (UV), capillary electrophoresis (CE), capillary electrochromatography (CEC), electrochemical, refractive index, and radioactivity detectors).

The reaction vessel having an internal diameter of less than about 2 mm may be a loop, which is a reaction vessel comprising a short tube, typically from 1 to 100 cm in length and more usually from 2-50 cm long. In general, the diameter of a loop is about 1 micrometre to 2 millimetres, preferably 40 to 200 micrometres.

Reaction vessels such as microfabricated devices and loops are particularly useful in radiochemistry. Conventional radiochemistry has been found to have a variety of disadvantages, including a requirement for large and expensive hot cells, inflexible rigs, significant loss of reagents during transfer between reaction vessels, which means that relatively large amounts of starting materials are required, HPLC purification and, in the case of $^{11}C$, low specific activity. However, by exchanging conventional reaction vessels for loops or microfabricated devices, the specific activity can be improved by an order of magnitude so that the amount of starting material, reagents and solvents can be significantly reduced and the crude product can be transferred into a vial or injected onto an HPLC column with minimal loss.

It is therefore preferred that the device to be coated by the method of the present invention comprises a device adapted to carry out a solid-phase radiochemical process.

Due to the radioactive nature of the process, such devices are provided with shielding to protect the operator from radioactive contamination. Such shielding suitably takes the form of a lead barrier or box around the device. Furthermore, the devices according to the invention are suitably connected to or incorporate a means of radiochemical detection, for example a positron detector or HPLC system fitted with a radioactivity detector.

A "solid phase radiochemical process" refers to a physical or chemical process in which one or more moieties taking part in the process is immobilised on a solid phase and in which one or more of the moieties taking part in the process comprises a radiotracer label.

One example of a solid phase radiochemical process is the recovery of a radioactive entity, for example the recovery of $^{18}$F-fluoride ion from $^{18}$O-enriched water containing $^{18}$F-fluoride ion or natural water containing $^{18}$F-fluoride ion.

The radioactive entity can either be eluted from the solid phase or can be used in situ in a further solid phase radiochemical process, for example an in situ labelling reaction such as a radiofluorination.

Another example of a solid phase radiochemical process is chromatographic separation in which analytes bind non-specifically to the solid support through a hydrophobic interaction and can be eluted by gradient elution using solvents of varying polarity. Yet another example of a solid phase radiochemical process is an enzymatic reaction in which the enzyme is immobilised on the solid phase.

The monomer or monomers used in the process will be chosen according to the purpose for which the device is required since the side chains of the polymer produced from the monomer will be used to bind to an immobilised reagent and the nature of the immobilised reagent will determine the nature of the side chains.

One type of monomer which is particularly suitable for use in the present invention is a monomer which can be polymerised by ring opening metathesis polymerisation (ROMP). Such a monomer is referred to in the present specification as a ROMP monomer and the product polymer is referred to as a ROMP polymer.

Coating the internal surfaces of devices with conventional polymers is often difficult since the presence of a radical or UV light is usually required to initiate polymerisation. Clearly this can present problems if the polymerisation is required to take place on the internal surface of a reaction vessel, and especially one with a narrow bore. In addition, most conventional polymers have low loading and limited swelling and this limits their usefulness as solid supports for chemical processes.

The ROMP reaction uses strained cyclic olefins to produce stereoregular and monodisperse polymers and co-polymers. The mechanism of ROMP reaction involves an ruthenium alkylidene catalyst (sometimes known as a Grubbs catalyst) and is identical to the mechanism of olefin synthesis except that, as the reaction involves a cyclic olefin, the new olefin that is generated stays attached to the catalyst as part of a growing polymer chain as illustrated below:

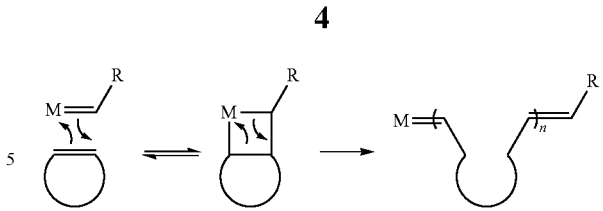

Wherein M is a metal selected from molybdenum and ruthenium and R is an organic substituent.

The driving force of the ROMP reaction is the relief of the strain on the ring such that the second step in the reaction above is essentially irreversible. Strained cyclic olefins such as those illustrated below have sufficient ring strain to make the reaction possible:

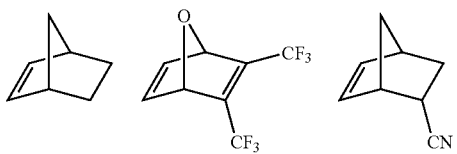

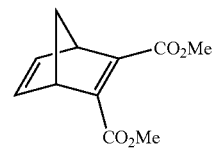

ROMP polymers have the advantage that they can be prepared from readily available and highly functionalised monomers and have high loading capacity. Furthermore, they can be prepared using a ruthenium carbene catalyst without the need for a radical or U.V. initiator and the viscosity of the monomer solution can be adjusted in order to influence the thickness of the polymer film.

Therefore, it is preferable that the monomer used in the method of the invention is a precursor or a ROMP polymer and that the solution also includes a ruthenium carbene catalyst.

When the one or more monomers are precursors of a ROMP polymer, the monomer solution also contains a cross-linker to control the amount of swelling of the ROMP polymer product. Increasing the amount of cross linker present in the monomer solution reduces the swelling seen in the final polymer and increases its rigidity. Optimal amounts of cross linker in the monomer solution are about 5-50 mol %. Suitable cross linkers are known in the art and one example of such a compound was used by Arstad et al, (Compound 5 in Org. Lett., 4(11), 1975-1977 (2002)) in the synthesis of a ROMP polymer-supported triphenylphosphine.

The degree of swelling of the ROMP polymer when exposed to solvents is thus easy to control and this is important since swelling of the polymer is necessary in order for it to react with compounds in solution, either to immobilise reagents on the polymer or for the reaction of the immobilised reagent. In addition, the swelling of the polymer allows extraction of the product from the reaction vessel by successive swelling and collapsing of the polymer coating.

A preferred ROMP polymer produced by the method of the present invention is of Formula (I):

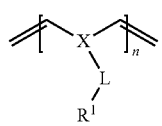

wherein:
X is either a $C_{4-6}$ cycloalkyl or $C_{4-6}$ heterocyclyl moiety;
L is a $C_1$ to $C_{20}$ linker group comprising one or more alkyl, alkenyl, alkynyl, $C_{4-10}$ cycloalkyl, $C_{4-10}$ heterocyclyl, $C_{4-10}$ aryl, $C_{4-10}$ heteroaryl, ether, PEG, sulphide, amide, sulphamide or a combination thereof; any of which may be substituted with one or more groups $R^2$
$R^1$ is hydrogen, $C_{1-20}$ alkyl, $C_{2-20}$ alkenyl, $C_{2-20}$ alkynyl, $C_{4-12}$ cycloalkyl, $C_{4-12}$ heterocyclyl, aryl, heteroaryl, $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$—$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$ or a group comprising an enzyme or a catalyst.
$R^2$ is $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$—$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$.
$R^3$ is H, OH, $C_{1-20}$ alkyl, $OC_{1-20}$ alkyl, $N(R^4)_2$, $N^+(R^4)_3$;
each $R^4$ is independently H or $C_{1-10}$ alkyl;
$R^5$ is $OR^4$, $SR^4$, $N(R^4)_2$, $N^+(R^4)_3$, $C_{4-10}$ cycloalkyl, $C_{4-10}$ heterocyclyl, aryl or heteroaryl;

In the present specification "alkyl" refers to a straight or branched saturated hydrocarbon chain optionally substituted with one or more halo substituents or with one or more $C_{3-7}$ cycloalkyl groups. "$C_{1-20}$ alkyl", for example, has one to twenty carbon atoms. Examples of alkyl groups include methyl, ethyl, n-propyl, isopropyl, t-butyl, n-hexyl, trifluoromethyl, 2-chloroethyl, methylenecyclopropyl, methylenecyclobutyl and methylenecyclopentyl.

In the present specification "cycloalkyl" refers to a saturated carbocyclic ring or to two or more fused carbocyclic rings. Examples of such groups include cyclopropyl, cyclobutyl, cyclopentyl and cyclohexyl. A $C_{4-6}$ cycloalkyl group has from 4 to 6 ring carbon atoms.

"alkenyl" refers to a straight or branched hydrocarbon chain containing one or more carbon-carbon double bonds and optionally substituted with one or more halo substituents or with one or more $C_{3-7}$ cycloalkyl groups.

"alkynyl" refers to a straight or branched hydrocarbon chain containing one or more carbon-carbon triple bonds and optionally substituted with one or more halo substituents or with one or more $C_{3-7}$ cycloalkyl groups.

"Heterocyclyl" refers to a cycloalkyl group in which one or more of the ring carbon atoms has been replaced by a nitrogen, oxygen or sulphur atom. Examples include tetrahydrofuran, morpholine, piperazine, and imidazoline.

In the present specification, "halo" refers to fluoro, chloro, bromo or iodo.

The terms "aromatic" and "aryl" in the context of the present specification refer to an aromatic ring system having from 4 to 14 ring carbon atoms and containing up to three rings. Examples of aromatic moieties are benzene, naphthalene and biphenyl.

"heteroaromatic" and "heteroaryl" refer to aromatic ring systems in which one or more of carbon atoms is replaced by a nitrogen, oxygen or sulphur atom. Examples of heteroaromatic moieties are pyridine, quinoline, isoquinoline, quinazoline, thiazole, benzthiazole, benzoxazole, benzimidazole, indole, indazole and imidazole ring systems.

$R^1$ is preferably halogen, OH, SH, $C_{1-20}$ alkyl, $C_{4-12}$ aryl, $C_{1-20}$ alkyl-$R^5$, $C_{1-20}$ alkyl-$C(O)R^3$, $N(R^4)_2$, $N^+(R^4)_3$ or a group comprising an enzyme or a catalyst.
where $R^3$ is OH, $R^4$ is as defined for general formula (I) and $R^5$ is $N(R^4)_2$, $N^+(R^4)_3$, aryl or heteroaryl;
$R^1$ is most preferably $C_{1-20}$ alkyl; —N=C=O, —SH or $N^+(R^4)_3$, particularly with bound $^{18}$F-fluoride ion or comprises an enzyme or a catalyst; and $R^4$ is as defined in general formula (I).

It is additionally suitable for more than one particular $R^1$ group to be present in the ROMP polymer product of the invention. This is achieved by the inclusion of more than one type of monomer in the reaction mixture and enables the swelling properties of the resultant polymer to be tailored as well as the production of a dual- or multi-capacity device.

A most preferred ROMP polymer produced by the method of the present invention is of Formula (II):

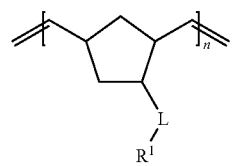

wherein:
-L-, $R^1$ and n are as defined above for Formula (I).

An especially preferred ROMP polymer of the present invention is of Formula (III):

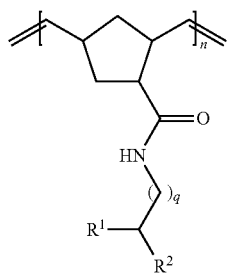

wherein:
$R^1$ and n are as defined above for Formula (I);
$R^2$ is an optional group as defined above for -L- of Formula (I); and,
q=1-4.

A most especially preferred ROMP polymer of the present invention is of Formula (III) wherein $R^1$ is trialkylammonium, $R^2$ is absent, q=3 and n=number of polymer units.

Devices coated with a ROMP polymer of Formula (III) are particularly suitable for the recovery of $^{18}$F-fluoride ion from $^{18}$O-enriched water containing $^{18}$F-fluoride ion, or natural water containing $^{18}$F-fluoride ion, as shown in Scheme 1 below:

Scheme 1

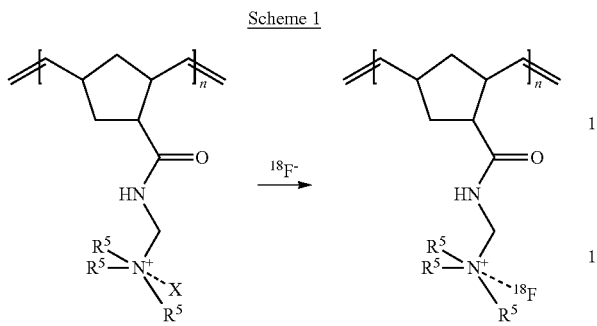

wherein each $R^5$ is independently a $C_{1-6}$ alkyl group and X is a non-nucleophilic anion, e.g. carbonate, bicarbonate or oxalate.

$R^1$ of Formula (III) then becomes trialkylammonium with bound $^{18}$F-fluoride ion, which renders the device particularly suitable for carrying out in situ radiofluoridations.

Preferably, the in situ radiofluoridation forms a step in the synthesis of an $^{18}$F-labelled radiotracer. The term "radiotracer" as used herein includes carrier-added and no carrier-added radiolabelled compounds, and in particular includes radioligands (compounds radiolabelled at high specific activity).

The skilled person will appreciate that use of other suitable R groups will enable immobilisation of other radiolabels of interest and their subsequent use for in situ radiolabelling reactions. Examples of other suitable radiotracer labels that can be immobilised for in situ radiolabelling reactions include: other non-metal positron emitters such as $^{11}$C, $^{13}$N, $^{15}$O, $^{17}$F, $^{75}$Br, $^{76}$Br or $^{124}$I; positron-emitting radioactive metals such as $^{64}$Cu, $^{48}$V, $^{52}$Fe, $^{55}$Co, $^{94m}$Tc or $^{68}$Ga; gamma-emitting radioactive halogens such as $^{123}$I, $^{125}$I, $^{131}$I or $^{77}$Br; and gamma-emitting radioactive metal ions such as $^{99m}$Tc.

Specific examples of $^{18}$F-labelled radiotracers which may be prepared using the ROMP polymer of Formula (III) where $R^1$ is trialkylammonium with bound $^{18}$F-fluoride ion, $R^2$ is absent, q=3 and n=number of polymer units, include: 2-[$^{18}$F] fluorodeoxyglucose (2-[$^{18}$F]-FDG); L-6-[$^{18}$F]fluoro-DOPA; 3'-deoxy-3'-fluorothymidine (FLT); 2-(1,1-dicyanopropen-2-yl)-6-(2-[$^{18}$F]fluoroethyl)-methylamino)-naphthalene ([$^{18}$F]FDDNP); 5[$^{18}$F]fluorouracil; 5[$^{18}$F]fluorocytosine; and, [$^{18}$F]-1-amino-3-fluorocyclobutane-1-carboxylic acid ([$^{18}$F]-FACBC). In each case, an unlabelled precursor compound of the $^{18}$F-labelled radiotracer is introduced into the device. $^{18}$F becomes incorporated into the precursor compound via nucleophilic substitution to form the $^{18}$F-labelled radiotracer as illustrated in Scheme 2.

Scheme 2

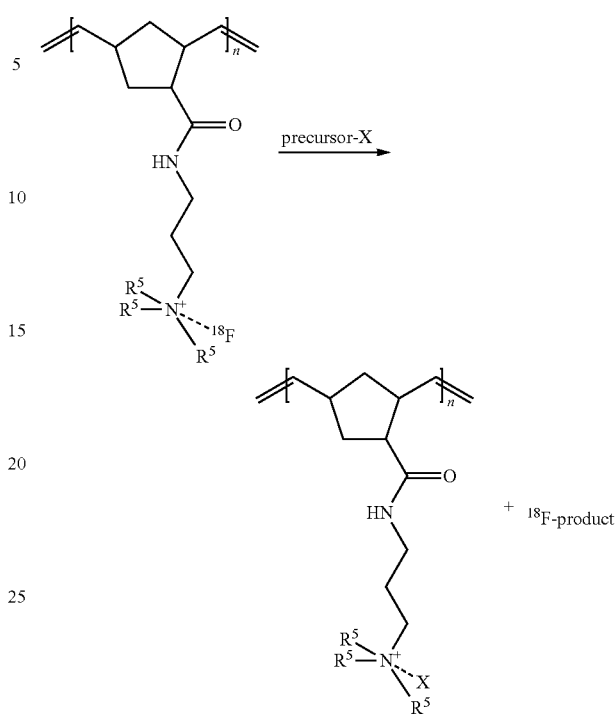

wherein each $R^5$ is independently a $C_{1-6}$ alkyl group and X is a non-nucleophilic anion, e.g. carbonate, bicarbonate or oxalate.

$R^1$ of Formula (III) then becomes trialkylammonium with bound $^{18}$F-fluoride ion, which renders the device particularly suitable for carrying out in situ radiofluoridations.

Preferably, the in situ radiofluoridation forms a step in the synthesis of an $^{18}$F-labelled radiotracer. The term "radiotracer" as used herein includes carrier-added and no carrier-added radiolabelled compounds, and in particular includes radioligands (compounds radiolabelled at high specific activity).

The skilled person will appreciate that use of other suitable R groups will enable immobilisation of other radiolabels of interest and their subsequent use for in situ radiolabelling reactions. Examples of other suitable radiotracer labels that can be immobilised for in situ radiolabelling reactions include: other non-metal positron emitters such as $^{11}$C, $^{13}$N, $^{15}$O, $^{17}$F, $^{75}$Br, $^{76}$Br or $^{124}$I; positron-emitting radioactive metals such as $^{64}$Cu, $^{48}$V, $^{52}$Fe, $^{55}$Co, $^{94m}$Tc or $^{68}$Ga; gamma-emitting radioactive halogens such as $^{123}$I, $^{125}$I, $^{131}$I or $^{77}$Br; and gamma-emitting radioactive metal ions such as $^{99m}$Tc.

The skilled person will also appreciate that although ROMP polymers are preferred, monomers which give rise to other types of polymer may also be used in the present invention and that the preferred side chains for such polymers are the same as those for the ROMP polymers discussed above.

In the process of the invention, each monomer may be present in the starting solution in a concentration of from about 0.1 to 5M, more usually about 0.5 to 2M and preferably about 1M.

Suitable solvents are polar aprotic organic solvents such as tetrahydrofuran and dichloromethane.

In some cases polymerisation can be initiated by heating. In other cases, however, particularly with some ROMP monomers, polymerisation may occur spontaneously at room temperature.

Monomers not containing hetero atoms capable of acting as ligands for the ruthenium metal core in the catalyst and that contains a bi-cyclic alkene are likely to polymerise spontaneously in the presence of the catalyst. Monomers not containing a bicyclic alkene and or containing hetero atoms that form complexes with ruthenium are likely to require heating.

When the device is a microfabricated device, the process of the invention may comprise the initial step of creating a defined network of channels within the device. This may be done using the following steps:

a) providing a suitable substrate;
b) marking a specific pattern onto the surface of said substrate;
c) etching the pattern into the surface of said substrate; and
d) attaching a cover to the etched surface of step (c) thereby forming channels.

Alternatively, it can comprise the use of a polymer in a process selected from injection moulding, hot embossing, casting, lithography or machining.

As discussed above, the process of the invention makes possible the production of devices comprising microfabricated devices or reaction vessels with an internal diameter of less than about 2 mm which have internal surfaces coated with a polymer.

Therefore in a further aspect of the invention, there is provided a device comprising a microfabricated device or a reaction vessel with an internal diameter of less than about 2 mm, wherein the internal surface is coated with a polymer substrate for a solid phase physical or chemical process.

It is preferred that the device is adapted for carrying out a solid phase radiochemical process.

Suitable polymers for coating the device are as described above in relation to the first aspect of the invention.

Devices of the invention may be fluidly interconnected to form an automated synthesis system and such a system forms a further aspect of the invention. A series of solid-phase radiochemical processes can be carried out within the system, e.g. a mixing and reaction device followed by an analysis device and finally a separation device. Such an automated synthesis system would enable the complete automation of a series of solid-phase radiochemical processes. This is desirable as it means (i) minimum user contact with radioactive reactants and (ii) the process takes as little time as possible thereby achieving a high specific activity product.

Devices of the invention which are adapted for carrying out solid phase radiochemical processes, for example the recovery of radioisotopes, radiochemical synthesis or radiochemical purification.

Examples of solid phase radiochemical processes which may be carried out using a device of the invention are the recovery of $^{18}$F-fluoride ion from $^{18}$O-enriched water containing $^{18}$F-fluoride ion and the preparation of a $^{18}$F-labelled radiotracer. In this case, it is particularly preferred that the polymer coating comprises a ROMP polymer of general formula (III) above, in particular a ROMP polymer of general formula (III) in which $R^1$ is trialkylammonium, $R^2$ is absent and q is 3.

Therefore in a further aspect of the invention, there is provided a method for recovering of $^{18}$F-fluoride ion from $^{18}$O-enriched water containing $^{18}$F-fluoride ion, the process comprising passing the $^{18}$O-enriched water containing $^{18}$F-fluoride ion through a device of the present invention in which the polymer coating comprises a ROMP polymer of general formula (III) in which $R^1$ is tri($C_{1-6}$ alkyl)ammonium, with a non-nucleophilic counter-ion, $R^2$ is absent and q is 3. The reaction is shown in Scheme 1 above.

$R^1$ of Formula (III) then becomes trialkylammonium with bound $^{18}$F-fluoride ion, which renders the device particularly suitable for carrying out in situ radiofluoridations.

Preferably, the in situ radiofluoridation forms a step in the synthesis of an $^{18}$F-labelled radiotracer. The term "radiotracer" as used herein includes carrier-added and no carrier-added radiolabelled compounds, and in particular includes radioligands (compounds radiolabelled at high specific activity).

The skilled person will appreciate that use of other suitable R groups will enable immobilisation of other radiolabels of interest and their subsequent use for in situ radiolabelling reactions. Examples of other suitable radiotracer labels that can be immobilised for in situ radiolabelling reactions include: other non-metal positron emitters such as $^{11}$C, $^{13}$N, $^{15}$O, $^{17}$F, $^{75}$Br, $^{76}$Br or $^{124}$I; positron-emitting radioactive metals such as $^{64}$Cu, $^{48}$V, $^{52}$Fe, $^{55}$Co, $^{94m}$Tc or $^{68}$Ga; gamma-emitting radioactive halogens such as $^{123}$I, $^{125}$I, $^{131}$I or $^{77}$Br; and gamma-emitting radioactive metal ions such as $^{99m}$Tc.

Specific examples of $^{18}$F-labelled radiotracers which may be prepared using the ROMP polymer of Formula (III) where $R^1$ is trialkylammonium with bound $^{18}$F-fluoride ion, $R^2$ is absent, q=3 and n=number of polymer units, include: 2-[$^{18}$F]fluorodeoxyglucose (2-[$^{18}$F]-FDG); L-6-[$^{18}$F]fluoro-DOPA; 3'-deoxy-3'-fluorothymidine (FLT); 2-(1,1-dicyanopropen-2-yl)-6-(2-[$^{18}$F]fluoroethyl)-methylamino)-naphthalene ([$^{18}$F]FDDNP); 5[$^{18}$F]fluorouracil; 5[$^{18}$F]fluorocytosine; and, [$^{18}$F]-1-amino-3-fluorocyclobutane-1-carboxylic acid ([$^{18}$F]-FACBC). In each case, an unlabelled precursor compound of the $^{18}$F-labelled radiotracer is introduced into the device. $^{18}$F becomes incorporated into the precursor compound via nucleophilic substitution to form the $^{18}$F-labelled radiotracer as illustrated in Scheme 2 above.

The structures of various $^{18}$F-labelled radiotracers and suitable precursors for their synthesis are given in Table I:

TABLE I

| $^{18}$F-labelled radiotracer | Precursor |
|---|---|
| 2[$^{18}$F]FDG | |

TABLE I-continued

| ¹⁸F-labelled radiotracer | Precursor |
|---|---|
| [¹⁸F]FLT | |
| [¹⁸F]FDDNP | |
| 5[¹⁸F]fluorouracil | |
| 5[¹⁸F]fluorocytosine | |
| [¹⁸F]-FACBC | |

In Table I above, OR* is a leaving group such as a sulphonate ester for example triflate or nonaflate and $P^1$—$P^4$ are each a protecting group. Suitable protection may be achieved using standard methods of protecting group chemistry. After the fluoridation is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc.

It will be appreciated by those skilled in the art that production of radiotracers may also be suitably carried out on a device wherein $R^1$ of Formulae I-III comprises the radiotracer precursor. Radiolabelling is achieved by introducing the radiolabel into the device, such that the radiolabelled product becomes detached from the polymer once radiolabelling has taken place successfully.

When $R^1$ of any of Formulas I to III is a $C_{1-20}$ alkyl group, the device is particularly suitable for performing chromatographic separations. A preferred side chain is a C18 hydrocarbon as this is the most commonly used side chain for reverse-phase chromatography, which is a chromatographic technique in which analytes bind non specifically through hydrophobic interaction. The bound analytes can be eluted by gradient elution using a solution of ever increasing or decreasing polarity.

When $R^1$ of any of Formulas I to III is a group comprising an enzyme, the device is particularly suitable for carrying out enzymatic reactions. With the enzyme immobilised on the ROMP polymer there is no necessity to have a separate step in the process for the removal of enzyme from the reaction mixture. An example reaction is the conversion of $^{11}$C-thymine to $^{11}$C-thymidine wherein thymidine phosphorylase is immobilised into the ROMP polymer. It will be appreciated that many other enzymatic reactions can be carried out in this way.

When $R^1$ of any of Formulas I to III is —SH, the device is particularly suitable as a scavenger, e.g. for taking up mercury ions from a solution.

BRIEF DESCRIPTION OF THE EXAMPLES

Example 1 describes the synthesis of ROMP monomer suitable for preparing a ROMP polymer for fluoride (ion-exchange) extraction.

Example 2 describes the synthesis of the cross-linker used in the reaction to polymerise the monomer prepared in Example 1.

Example 3 describes the synthesis of tertiary amine ROMP polymer.

The results of Example 4 show that the synthesized ROMP resin can be used for the successful removal of $^{18}$F-fluoride from aqueous media (such as that obtained from the cyclotron target). Furthermore the fluoride can be removed from the resin (in yields of up to 80%) by flushing the resin with $K_2CO_3$ (aq). Lastly it has been shown that the performance of the ROMP resin is at least equivalent if not superior to what is arguably the industrial standard solid phase for this application.

Example 5 relates to the cartridge testing of ROMP fluoride extraction polymer for extraction of fluoride from target water.

Example 6 describes a process for the production of $[^{18}F]$ FDG on a microfabricated device.

Example 7 relates to the creation of a predetermined network of microchannels on the surface of a glass, silicon or polymer substrate.

Example 8 relates to coating the surfaces of a microfabricated device with ROMP polymer having trialkylammonium side chains.

Example 9 describes a process used for the recovery of $[^{18}F]$fluoride from $^{18}$O-enriched water using the device of the present invention.

In the Examples the following abbreviations are used:
RT room temperature
DCM dichloromethane
THF tetrahydrofuran
TLC thin layer chromatography
HPLC high performance liquid chromatography

EXAMPLE 1

Figure 1:
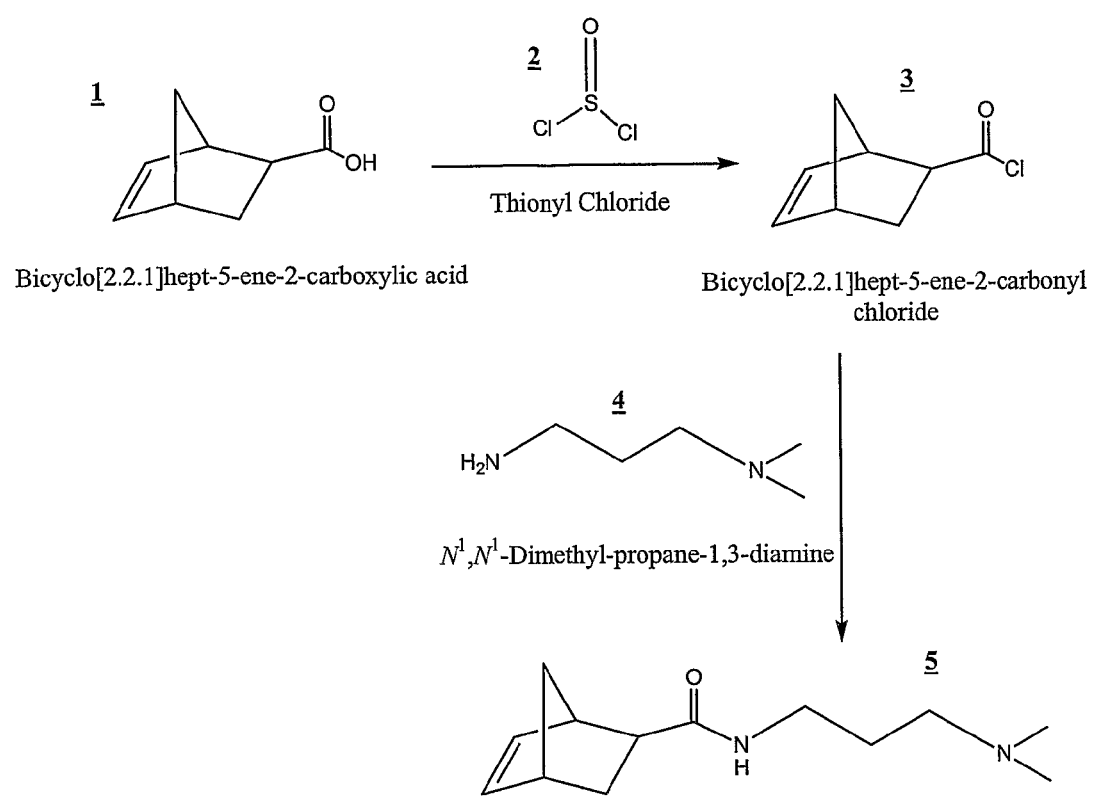
FIG. 1 illustrates the reaction scheme used for synthesis of ROMP monomer for fluoride (ion-exchange) extraction.

Synthesis of ROMP Monomer for Fluoride (Ion-Exchange) Extraction the Reaction Scheme is Illustrated in FIG. 1

(a) Preparation of Acid Chloride

To 10 g (72 mMol) of Norbornene carboxylic acid 1 was added 10.4 ml of thionyl chloride 2 (17 g or 144 mMol). The mixture was stirred under a nitrogen atmosphere for 2 hours (Reaction mixture is a clear champagne-coloured liquid).

Excess thionyl chloride was then removed on a rotary evaporator by the addition of aliquots (4×6 ml) of toluene at approximately 45° C. The acid chloride 3 could be stored for up to a week before use providing it was kept refrigerated and under nitrogen.

(b) Reaction of Acid Chloride with Amine

To the acid chloride 3 was added 15 ml DCM and the mixture chilled on ice. 0.8 equivalents (5.92 g, 58 mMol, 7.3 ml) of amine 4 were then added drop-wise with stirring. The reaction mixture was then allowed to reach RT and left to react for a further two hours. This entire procedure was performed under a nitrogen atmosphere (After amine addition reaction mixture appears as an opaque honey colour solution containing white precipitate).

(c) Purification of Crude Monomer Mixture

After the two hours reaction time the reaction mixture was extracted with 3×10 ml of 30% v/v conc. $H_3PO_4$ (pH ~2). The combined aqueous components were then adjusted to pH 12 using conc. NaOH(aq) and extracted with 4×12 ml DCM. The combined DCM fragments were dried over $MgSO_4$, filtered and the DCM removed under reduced pressure to yield the purified monomer 5 (11.2 g heavy golden oil, 87%).

Elemental C:H:N analysis gave 64.99% C, 9.34% H and 11.30% N. (expected values calculated from $C_{13}H_{22}N_2O$, formula weight=222 were 70.23% C, 9.97% H and 12.60% N).

EXAMPLE 2

Synthesis of Cross-Linker

Figure 2:
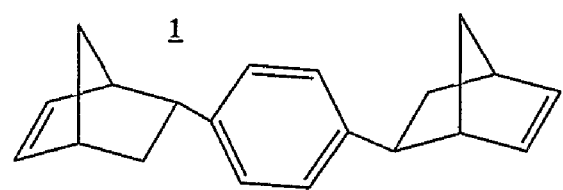
FIG. 2 shows the chemical structure of the synthesised cross-linker.

FIG. 2 shows the chemical structure of the synthesised cross-linker.

To a stirred solution of 1,4-Diiodo-benzene (9.90 g, 30 mMol), norbornadiene (35 ml, 325 mMol), piperidine (14.9 ml, 50 mMol) and $(AcO)_2(PPh_3)_2Pd(II)$ (0.674 g, 3 mMol) in DMF (45 ml) was added dropwise formic acid (3.46 ml, 63 mMol). A considerable amount of heat was evolved and the mixture went into solution. The reaction was followed using TLC (hexane mobile phase on silica, Rf(cross linker)=0.5). Spots were elucidated using UV. After 41 hrs the reaction was quenched with water (200 ml) and the resulting mixture extracted with hexane (4×100 ml). The combined organic phase was washed with 10% NaOH (3×100 ml), 10% $H_3PO_4$ (3×100 ml), water (3×100 ml) and saturated brine (1×100 ml). The organic phase was then dried over $MgSO_4$ and concentrated to give a dark red oil.

Purification was achieved in two stages via silica chromatography (hexane). A short primary column removed the dark red impurity (Rf=0-0.1) to give a colourless oil. Further purification on a larger column yielded 3.64 g of a white solid 1 (46%).

Mass spectrometry (EI+ve mode) of the product gave a peak at m/z=262 $[M]^+$. Elemental C:H analysis gave 91.51% C and 8.63% H (expected values calculated from $C_{20}H_{22}$, formula weight=262 were 91.55% C, 8.45% H). $^1$H-NMR in $CDCl_3$, δ(ppm) relative to tetramethylsilane (TMS): 7.2 (s, 4H, Aryl-CH), 6.2 (d m, 4H, Vinyl-CH), 2.95 (broad s, 2H, allylic-CH), 2.88 (broad s, 2H, allylic-CH), 2.7 (m, 2H, benzylic-CH).

EXAMPLE 3

Synthesis of Tertiary Amine ROMP Polymer

Figure 3:
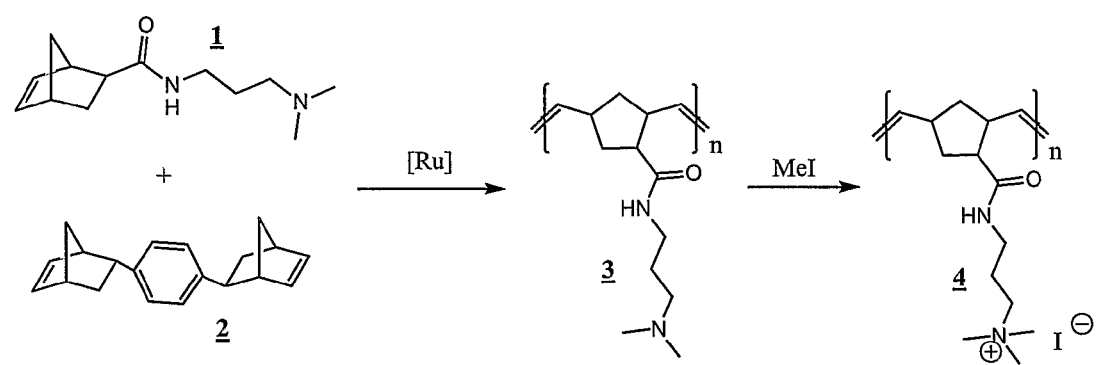
FIG. 3 illustrates the reaction scheme used for synthesis of tertiary amine ROMP polymer.

FIG. 3 illustrates the reaction scheme used for synthesis of tertiary amine ROMP polymer.

To a 50 ml round bottom flask was added monomer 1 (2 g, 9 mMol), cross linker (0.262 g, 1 mMol), THF (12 ml) and DCM (2 ml). The contents of the flask were then mixed thoroughly and flushed with nitrogen. To this solution was added catalyst (0.09 g, ~1%) in DCM (1 ml) and again the contents mixed. The static reaction mixture was then left under an inert atmosphere at 40° C. for one hour.

After one hour the crude resin product (translucent brown gel) was broken into several fragments with a spatula and 20 ml of the following mixture was added: 75% THF, 20% $CH_3CN$ and 5% Ethyl Vinyl Ether. A condenser was then fitted and the mixture was refluxed at 120° C. under nitrogen for 1 hr. The resin was then transferred to a glass funnel with a frit and washed with sequential THF (20 ml) followed by diethyl ether (20 ml) a total of three times before being dried under vacuum. The dried resin product 3 appears as a mottled brown solid (see FIG. 3) (1.79 g, 79%, theoretical loading 3.98 mMol/g).

For production of the quaternary ammonium salt polymer 4, polymer 3 (1 g) was added to methyl iodide (10 equivalents, 39.8 mMol, 5.65 g, 2.5 ml), THF (16 ml) and DCM (10 ml) and refluxed (85° C.) under a nitrogen atmosphere for 1 hr. The polymer was then transferred to a glass funnel with frit and washed with DCM (3×20 ml) and diethyl ether (3×20 ml) before being dried under vacuum (1.44 g, 92%).

Elemental C:H:N:I analysis gave: 50.64% C, 7.48% H, 5.77% N and 27.34% I (expected values calculated from a "theoretical" monomer unit of $C_{14.44}H_{24.78}N_{1.85}O_{0.93}I_{0.93}$, formula weight=356.5 were: 48.66% C, 6.95% H, 7.22% N, and 32.95% I).

EXAMPLE 4

Testing of ROMP Fluoride Extraction Polymer for Extraction of Fluoride from Target Water 1.5 ml of aqueous $^{18}$F-fluoride (i.e. mixture direct from target) measuring approximately 3 MBq (3 mCi) was loaded into a 2.5 ml plastic funnel (Mobitec column, see FIG. 4B) containing 0.1 g resin and the mixture agitated for 40 minutes. A further three additional funnels containing silica, tertiary amine resin (1 FIG. 4A) and solid phase removed from a Waters Accell™ QMA Sep-Pack (3 FIG. 4A) were also loaded with aqueous $^{18}$F-fluoride and treated analogously. These served as a control and two comparison groups respectively. After agitation the columns were purged of liquid and flushed with water (3×1 ml). Both the radioactivity retained on the solid phase as well as that flushed from the funnel was measured.

A representative set of results is shown in the table below.

| Solid phase | Activity retained on resin after water wash. | Activity retained on resin after wash with 1M $K_2CO_3$ (aq) |
|---|---|---|
| Tertiary amine 1 | 45% | — |
| quaternary-ammonium resin 2 | 91% | 22% |
| QMA resin 3 | 94% | 5% |
| Silica | 7% | — |

Though the above results established resin function, direct comparisons of extraction efficiency between resins 2 and 3 (FIG. 4A) were approximate due to the difference in respective counter ions (iodide & chloride respectively). To remedy this, the experiment was repeated with the QMA and quaternary ammonium resins after they were each conditioned with 1M $K_2CO_3$ (3×1 ml) and water (3×1 ml). This meant that both resins were in the carbonate form were by a direct comparison could be made. The table below shows a set of representative results.

| Solid phase | Activity retained on resin after water wash. | Activity retained on resin after wash with 1M $K_2CO_3$ (aq.) |
|---|---|---|
| quaternary-ammonium carbonate resin | 39% | 24% |
| QMA carbonate resin | 14% | 28% |

Figure 4:
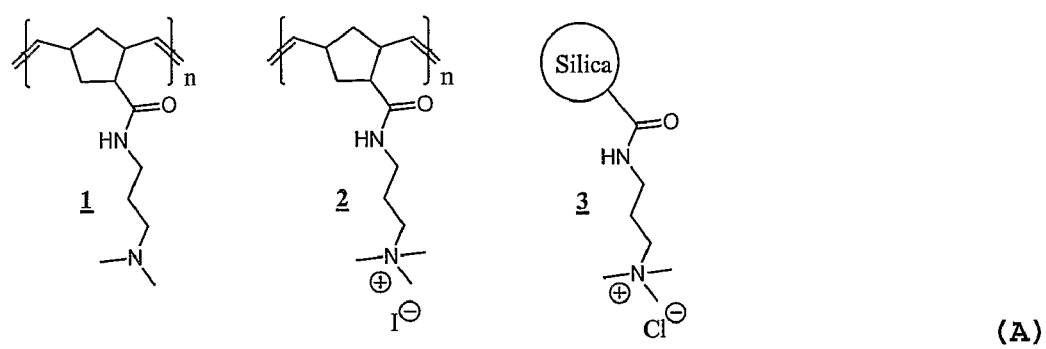
FIG. 4A illustrates the chemical structures of tertiary amine resin, quaternary-ammonium resin, and QMA resin.
FIG. 4B illustrates the set up used for testing ROMP fluoride extraction polymer for extraction of fluoride from target water.
FIG. 4C shows the extraction of $^{18}$F-fluoride from aqueous media via the process of ion-exchange.
Figure 4:
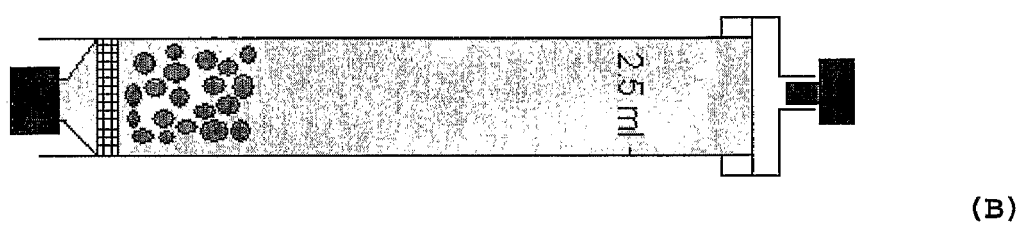
Figure 4:
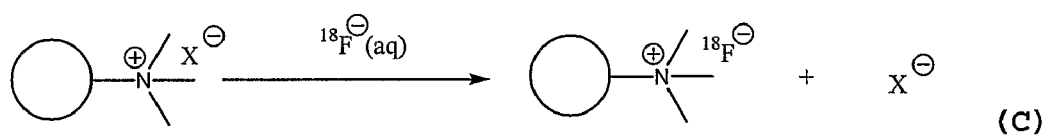

Extraction of $^{18}$F-fluoride from aqueous media is achieved via the process of ion-exchange as shown in FIG. 4C.

EXAMPLE 5

Figure 5:
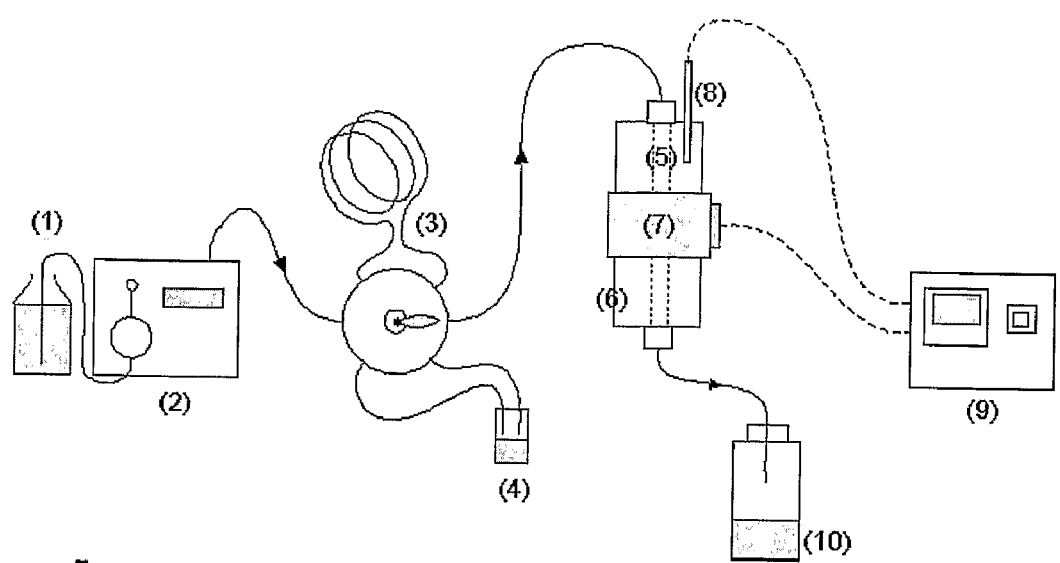
FIG. 5 illustrates the set up for conducting cartridge testing of ROMP fluoride extraction polymer for extraction of fluoride from target water.

Cartridge Testing of ROMP Fluoride Extraction Polymer for Extraction of Fluoride from Target Water The set up for conducting this experiment is illustrated in FIG. 5. The set up consists of a HPLC pump (2) that supplies a continuous flow of acetonitrile (1) through a HPLC injection valve (3) and onto the column containing the resin (5). Reagents including: water, $K_2CO_3$ (aq) and aqueous $^{18}$F-fluoride are contacted with the resin by loading onto a 2 ml stainless steel loop before being injected (as a liquid plug) into the acetonitrile stream by switching the valve. Liquid output from the column and waste from the loop are collected in containers (10) and (4) respectively. The column can be heated to a preset temperature using a heating system, made up of a moulded aluminium block (6), a thermocouple (8), a band heater (7) and a temperature controller (9). The resin is kept within the column (5) using PTFE frits (filter discs) at both the column input and column output.

The basic fluoride extraction/recovery experiment conducted on the column proceeded as follows. Dry ammonium resin (chloride salt) (0.15 g) was loaded onto the column and the system assembled. The HPLC pump was then set to administer a continuous flow of acetonitrile at a flow rate of 0.5 ml/min. At this flow rate the resin was conditioned with plugs of $K_2CO_3$ 0.5 M (3×2 ml) and water (3×2 ml) each injected via the loop/HPLC valve. The acetonitrile flow was then reduced to 0.2 ml/min and 18F-fluoride approximately 370 MBq (10 mCi) made up to 1 ml with water was injected onto the column. After 15 min the flow was increased to 0.5 ml/min for a further 5 minutes after which the Radioactivity in the collection vial (10) was measured. The percentage activity that passed through the column without being extracted was consistently <1%. Next the output vial (10) was refreshed and the resin flushed with 2 ml of $K_2CO_3$ 0.5M at 0.5 ml/min. This step exchanged the fluoride immobilized on the resin with carbonate causing the radioactivity to leave the column and be recovered in the collection vial. Using this method it was possible to retain fluoride on the resin and then subsequently recover it into 0.5 M $K_2CO_3$ (2 ml) at efficiencies averaging 98%.

EXAMPLE 6

Production of [$^{18}$F]FDG on a Microfabricated Device

Figure 6:
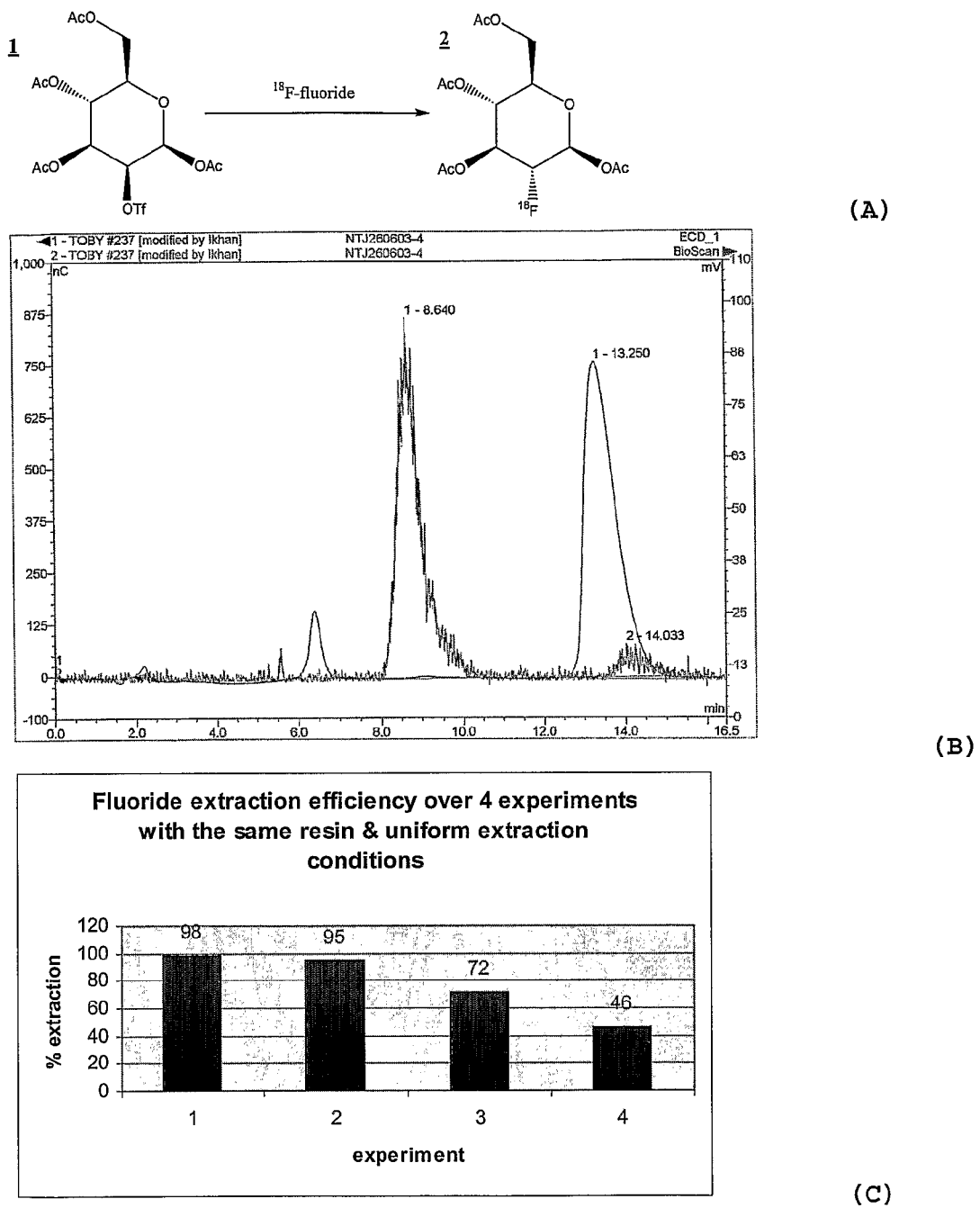
FIG. 6A illustrates the radiofluoridation of the precursor of $[^{18}F]$-FDG. Ac represents an acyl protecting group.
FIG. 6B illustrates a sample radio-HPLC trace of the radiochemical composition of the collection vial contents obtained following radiofluoridation of the precursor of $[^{18}F]$-FDG on a microfabricated device.
FIG. 6C illustrates the change in behaviour of the resin over time (despite conditioning prior to each experiment) and a trend to ever less efficient fluoride extraction.

The method for extracting the fluoride onto the resin was achieved as detailed in Example 5. Having injected the aqueous fluoride onto the column (t=0 min) at 0.2 ml/min over a period of 15 min, the column was heated to 100° C., for a further 15 minutes while maintaining the flow of acetonitrile. This procedure was designed to azeotropically remove all water from the column. Then at t=30 min the loop was flushed with anhydrous acetonitrile and the set temperature reduced to 75° C. On attainment of the set temperature (t=X min ) a solution of 1 (20 mg in 1 ml $CH_3CN$; FIG. 6A) was loaded onto the loop and injected onto the column. Lastly at t=X+20 the column was flushed with $K_2CO_3$ (aq) 0.5 M (2M). This procedure is summarized in the time-line shown below.

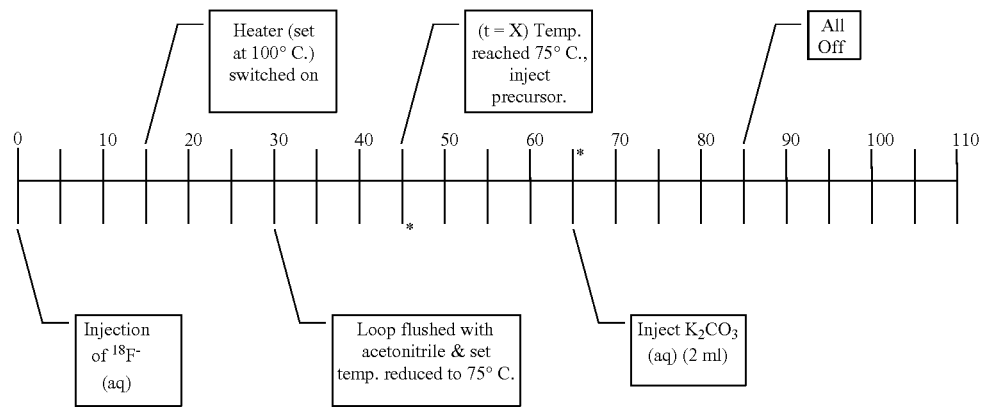

The horizontal scale is in minutes, along which are marked the various operations. The '*' marks denote points when the column output vial was refreshed. Note also that the entire process is conducted with a continuous flow of acetonitrile (0.2 ml/min).

Less than 2% of the overall radioactivity eluted from the column (/resin) prior to introduction of the $K_2CO_3$ (aq). With the introduction of $K_2CO_3$ (aq) onto the resin the radioactivity was almost quantitatively eluted into the collection vial (ca 99%). The radiochemical composition of the collection vial contents was then determined using radio-HPLC. See sample trace in FIG. 6B.

Over the course of 4 experiments using the same resin sample a greater percentage of the activity was seen to elute from the column prior to the base flush. By the 4th experiment this percentage had grown to approximately half the total activity. This change in behaviour was associated with a discolouration of the resin (despite conditioning prior to each experiment) and a trend to ever less efficient fluoride extraction (see FIG. 6C).

EXAMPLE 7

Figure 7:
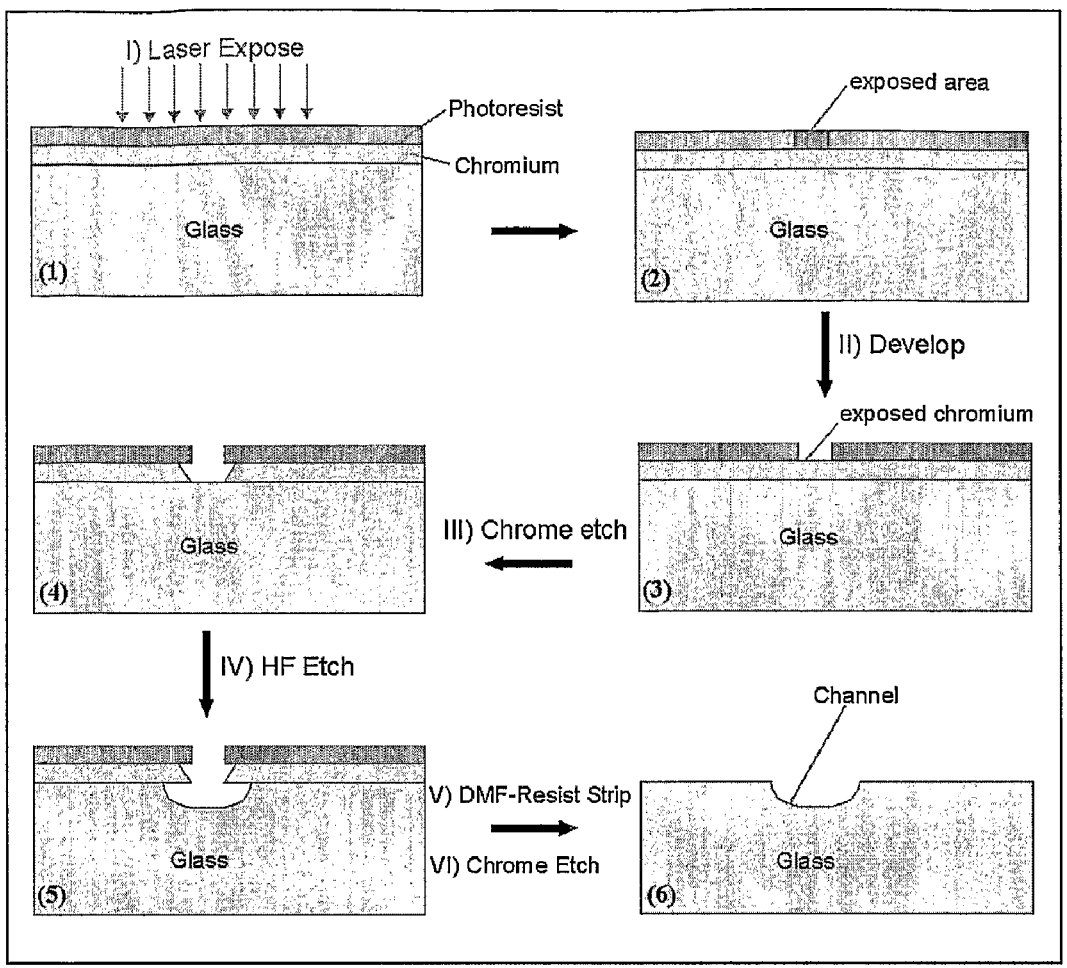
FIG. 7 illustrates the steps involved in the creation of a predetermined network of microchannels on the surface of a glass, silicon or polymer substrate.

Creation of a Predetermined Network of Microchannels on the Surface of a Glass, Silicon or Polymer Substrate FIG. 7 illustrates the steps involved in the creation of a predetermined network of microchannels on the surface of a glass, silicon or polymer substrate.

Masks made using a direct write lithography system were used to shadow cast (expose) substrates. After shadow casting, the exposed area of photoresist and subsequently chromium were selectively removed. Next etching using an aqueous solution 5% (7:1 $NH_3F$:HF), 9.25% HCl were used to create open channels (etch rates of 0.2 μm min-1) of 50 μm depth. Following etching, both resist and chromium layers were removed. To complete the process a pre-drilled cover plate (microscope slide) and etched substrate were sonicated in DMF, acetone and methanol (2 min each) and immersed in conc. sulphuric acid (2 hrs). Further washing with ultra pure water and drying under a flow of nitrogen, preceded loading of the furnace. Thermal bonding used a 12 hr ramped temperature programme with a maximum temperature of 600° C.

76 mm Low Reflective Chrome (Cr 1000⊕), print grade sensitised, Soda Lime glass substrates of thickness 0.01" and 0.06" were purchased from Nanofilm (Westlake Village, Canada). Clear Soda-lime glass microscope slide 26 mm×75 mm×1 mm, hydrochloric acid (HCl), acetone, methanol, ammonium fluoride solution (NH4F), hydrofluoric acid (HF) and sulphuric acid ($H_2SO_4$ sp.gr. 1.84) were purchased from BDH. Dimethylformamide (DMF) was purchased from Aldrich. Shipley's Microposit 351 developer and Shipley's chrome etchant 18 were purchased through Chestech Ltd. (Chestech Ltd., Rugby, Warwickshire, UK). Teflon tubing 1.6 mm (1/16") o.d. 380 μm i.d. was supplied by Upchurch Scientific. GlasSeal Connectors, 1.6 mm (1/16") steel unions, peek fingertight fittings and fused silica capillary (375 μm o.d.) were supplied by Supelco. Araldite 2014 epoxy was supplied by RS-Components.

Chip design was done on a PC running AutoCad LT for Windows 95. The Direct Write Laser system was a prototype DWLII system from Heidelberg Instruments (Heidelberg Instruments Mikrotechnik GmbH, 69126 Heidelberg, Germany). Furnace used for glass bonding were Thermicon P (Heraeus) instruments.

EXAMPLE 8

Coating the Surfaces of a Microfabricated Device with ROMP Polymer Having Trialkylammonium Side Chains A solution of the monomer Compound 1 (FIG. 8), crosslinker and catalyst in tetrahydrofuran was introduced into the device, which was heated using a chromium electrode and an applied voltage of 120 V (~80° C.) to allow polymerisation to occur on the internal surfaces of the device. At the same time a stream of nitrogen was flowed through the microchannels such that the polymer did not block the microchannels (FIG. 9). The nitrogen supply was at 1.5 Bar (1-2 ml/min approx) and the liquid flow was 5-10 μl/min. The width of the microchannel (not that defined by the gas flow) was 150 μm.

Figure 10:
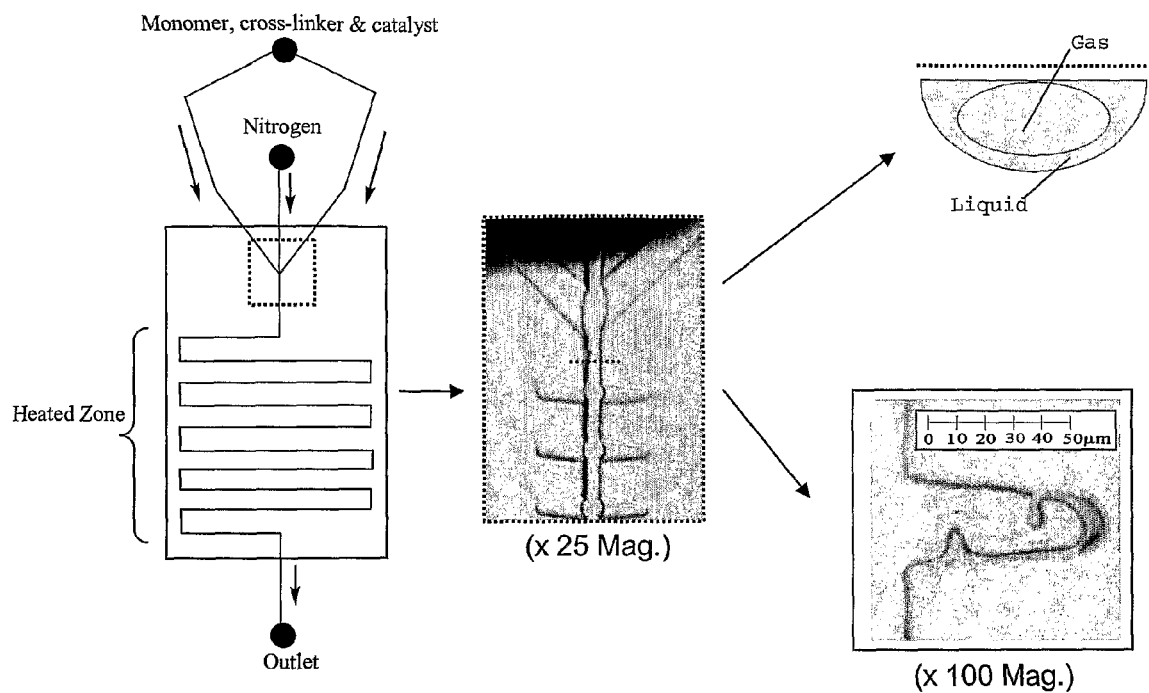
FIG. 10 shows a schematic of a microfabricated device as well as micrographs at ×25 and ×100 of the microchannels coated with ROMP polymer.

FIG. 10 shows a schematic of a microfabricated device as well as micrographs at ×25 and ×100 of the microchannels coated with ROMP polymer.

Figure 8:
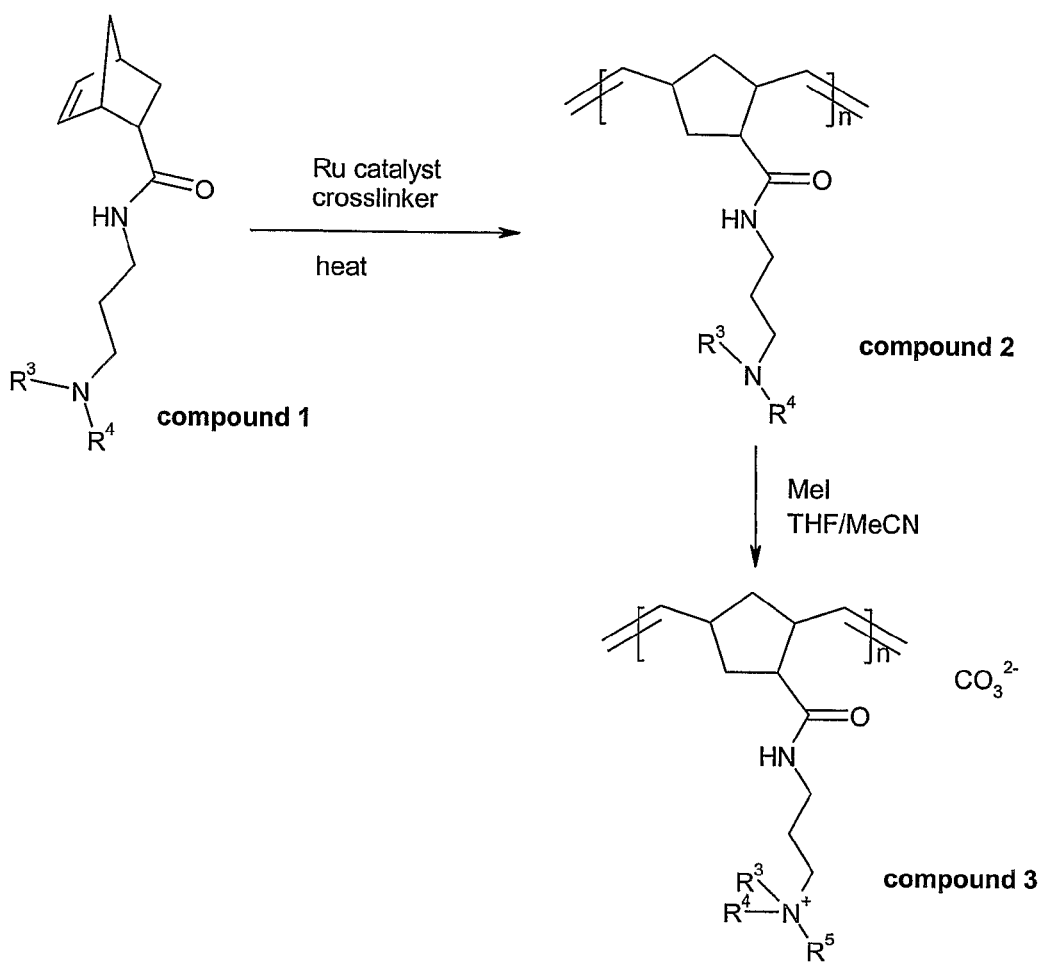
FIG. 8 shows the synthesis of a ROMP polymer having a trialkylammonium side chain, wherein $R^3$ to $R^5$ are independently $C_{1-6}$ alkyl groups.
Figure 9:
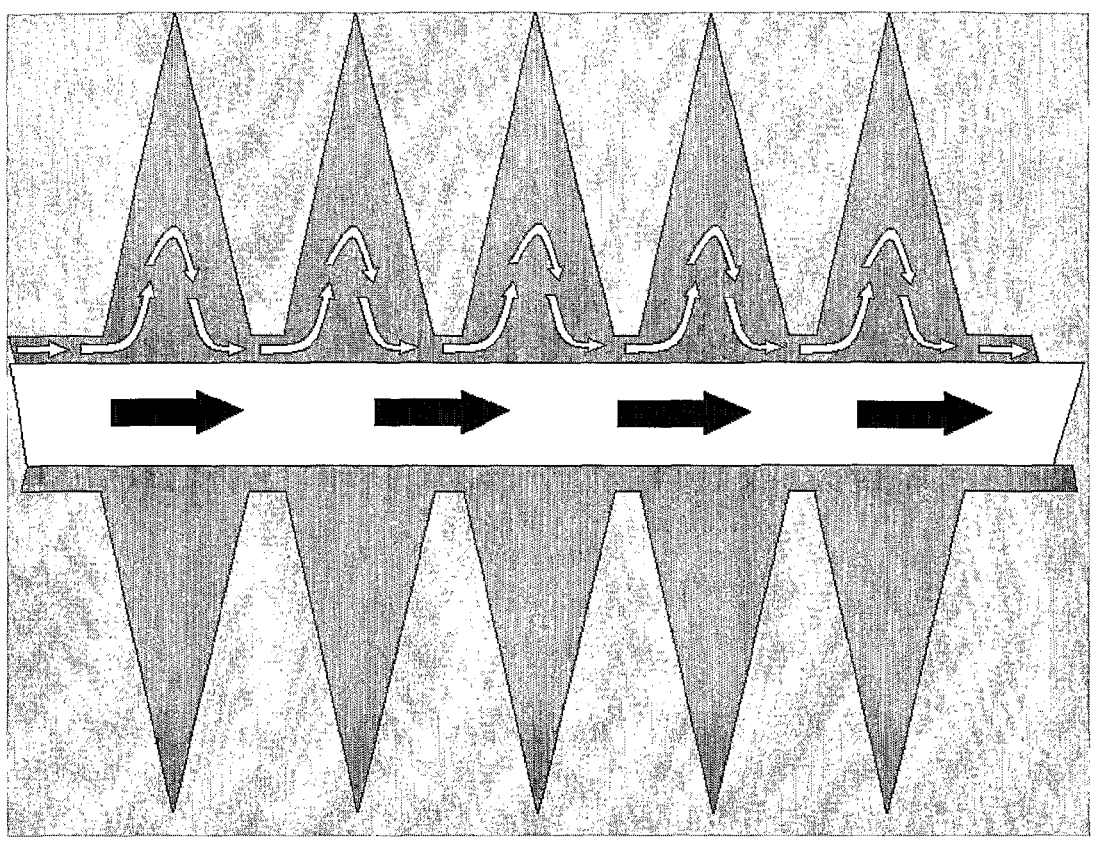
FIG. 9 is a schematic diagram showing how the polymerisation is carried out in the microchannels of a microfabricated device. The centre flow (white) is the gas (from a regulated cylinder) and the liquid flow (black) through the side indentations(from syringe pumps) is the ROMP polymer reaction mixture

The dialkylammonium group on the polymer (compound 2) was then converted to a trialkylammonium group (compound 3) in situ by methylation as shown in FIG. 8.

EXAMPLE 9

Recovery of [$^{18}$F]fluoride from $^{18}$O-Enriched Water

Figure 11:
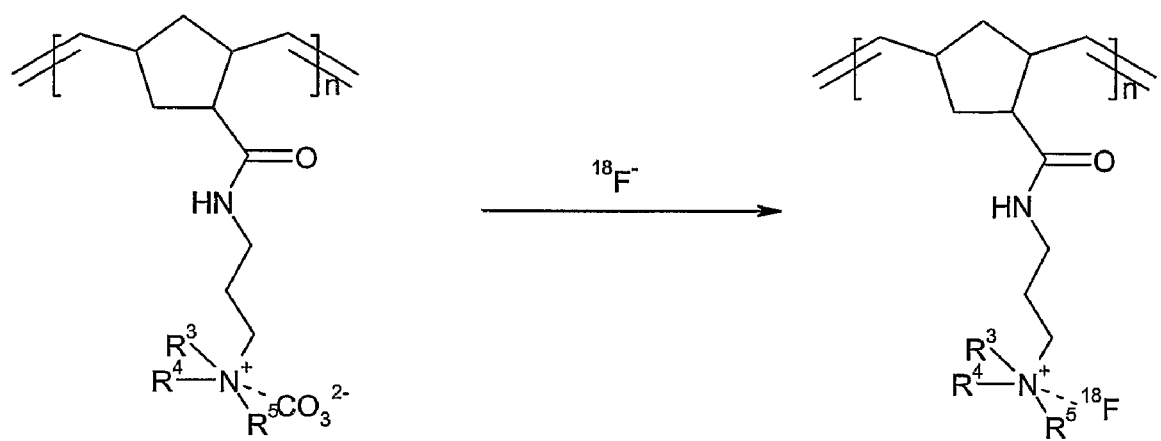
FIG. 11 illustrates retention of [18F]-fluoride on the polymer on a microfabricated device through ion exchange following introduction of an aqueous solution of $[^{18}F]$fluoride. $R^3$ to $R^5$ are independently $C_{1-6}$ alkyl groups.

Into the device prepared according to Example 8 was introduced an aqueous solution of [$^{18}$F]fluoride. As this passed through the microchannels the [$^{18}$F]fluoride was retained on the polymer through ion exchange (as illustrated in FIG. 11) and enriched water was recovered from the exit port of the device.

The polymer can be dried by passing anhydrous acetonitrile through the microchannels with heating.

What is claimed is:

1. A method of coating the internal surface of a device with a polymer, wherein the device is a microfabricated device or a reaction vessel with an internal diameter of less than about 2 mm, the method comprising the steps of:
   (i) introducing into the device a solution of one or more monomers in a suitable solvent;
   (ii) introducing a flow of an inert gas through the device; and
   (iii) initiating polymerisation of the monomer solution;
   wherein polymerisation of the one or more monomers leads to a ROMP polymer of Formula (I):

wherein:
X is either a $C_{4-6}$ cycloalkyl or $C_{4-6}$ heterocyclyl moiety;
L is a $C_1$ to $C_{20}$ linker group comprising one or more alkyl, alkenyl, alkynyl, $C_{4-10}$ cycloalkyl, $C_{4-10}$ heterocyclyl, $C_{4-10}$ aryl, $C_{4-10}$ heteroaryl, ether, PEG, sulphide, amide, sulphamide or a combination thereof; any of which may be substituted with one or more groups $R^2$
$R^1$ is hydrogen, $C_{1-20}$ alkyl, $C_{2-20}$ alkenyl, $C_{2-20}$ alkynyl, $C_{4-12}$ cycloalkyl, $C_{4-12}$ heterocyclyl, aryl, heteroaryl, $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$-$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$ or a group comprising an enzyme or a catalyst;
$R^2$ is $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$-$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$;
$R^3$ is H, OH, $C_{1-20}$ alkyl, $OC_{1-20}$ alkyl, $N(R^4)_2$, $N^+(R^4)_3$;
each $R^4$ is independently H or $C_{1-10}$ alkyl;
$R^5$ is $OR^4$, $SR^4$, $N(R^4)_2$, $N^+(R^4)_3$, $C_{4-10}$ cycloalkyl, $C_{4-10}$ heterocyclyl, aryl or heteroaryl.

2. A method as claimed in claim 1, wherein the inert gas is nitrogen or argon.

3. A method as claimed in claim 1, wherein the device is a microfabricated device or a loop from 1 to 100 cm in length.

4. A method as claimed in claim 1, wherein the device is adapted to carry out a solid-phase radiochemical process.

5. A method as claimed in claim 1 wherein polymerisation of the one or more monomers leads to a ROMP polymer of Formula (II):

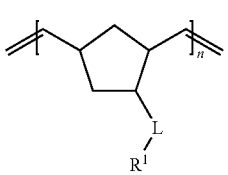
(II)

wherein:

-L-, $R^1$ and n are as defined above for Formula (I).

6. A method as claimed in claim 1 wherein polymerisation of the one or more monomers leads to a ROMP polymer of Formula (III):

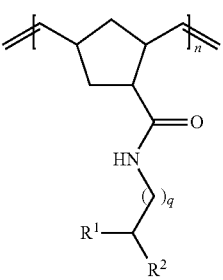
(III)

wherein:

$R^1$ and n are as defined above for Formula (I);

$R^2$ is an optional group as defined above for -L- of Formula (I); and, q =1-4.

7. A method as claimed in claim 6, wherein, in the ROMP polymer of Formula (III), $R^1$ is trialkylammonium, $R^2$ is absent, q =3 and n =number of polymer units.

8. A method as claimed in claim 1, wherein each monomer is present in the starting solution in a concentration of from about 0.1 to 5M.

9. A method as claimed in claim 1 wherein, in the monomer solution, the solvent is a polar aprotic solvent.

10. A method as claimed in claim 1 wherein polymerisation is initiated by heating.

11. A method as claimed in claim 1 wherein polymerisation occurs spontaneously.

12. A method as claimed in claim 1, wherein the device is a microfabricated device and, the process of the invention comprises the initial step of creating a defined network of channels within the device.

13. A device comprising a microfabricated device or a reaction vessel with an internal diameter of less than 2 mm, wherein the internal surface is coated with a polymer of Formula (I):

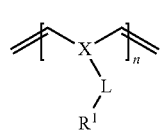
(I)

wherein:

X is either a $C_{4-6}$ cycloalkyl or $C_{4-6}$ heterocyclyl moiety;

L is a $C_1$ to $C_{20}$ linker group comprising one or more alkyl, alkenyl, alkynyl, $C_{4-10}$ cycloalkyl, $C_{4-10}$ heterocyclyl, $C_{4-10}$ aryl, $C_{4-10}$ heteroaryl, ether, PEG, sulphide, amide, sulphamide or a combination thereof; any of which may be substituted with one or more groups $R^2$ $R^1$ is hydrogen, $C_{1-20}$ alkyl, $C_{2-20}$ alkenyl, $C_{2-20}$ alkynyl, $C_{4-12}$ cycloalkyl, $C_{4-12}$ heterocyclyl, aryl, heteroaryl, $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$-$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$ or a group comprising an enzyme or a catalyst;

$R^2$ is $C(O)R^3$, $C_{1-20}$ alkyl-$C(O)R^3$, $C_{2-20}$ alkenyl-$C(O)R^3$, $C_{2-20}$ alkynyl-$C(O)R^3$, nitro, isocyanate, $C_{1-10}$ alkyl-$C(O)$—$C(R^4)_2$-$C(O)$—$C_{1-10}$ alkyl, aminooxy, nitrile, phosphorus chloride, succinimide, sulphonyl chloride, halogen, tosylate, mesylate, triflate, nonaflate, silane, $OR^4$, $SR^4$, $N(R^4)_2$, $N^+(R^4)_3$, quaternary phosphorous, $C_{1-20}$ alkyl-$R^5$, $C_{2-20}$ alkenyl-$R^5$ or $C_{2-20}$ alkynyl-$R^5$;

$R^3$ is H, OH, $C_{1-20}$ alkyl, $OC_{1-20}$ alkyl, $N(R^4)_2$, $N^+(R^4)_3$, each $R^4$ is independently H or $C_{1-10}$ alkyl;

$R^5$ is $OR^4$, $SR^4$, $N(R^4)_2$, $N^+(R^4)_3$, $C_{4-10}$ cycloalkyl, $C_{4-10}$ heterocyclyl, aryl or heteroaryl.

14. A device as claimed in claim 13 adapted for carrying out a solid phase radiochemical process.

15. An automated synthesis system comprising two or more devices as claimed in claim 13 which are fluidly interconnected.

16. A method for recovering of $^{18}$F-fluoride ion from $^{18}$O-enriched water containing $^{18}$F-fluoride ion, the process comprising passing the $^{18}$O-enriched water containing $^{18}$F-fluoride ion through a device as claimed in claim 13 or a system comprising two or more devices as claimed in claim 13 which are fluidly interconnected, in which the polymer coating comprises a ROMP polymer of general formula (III):

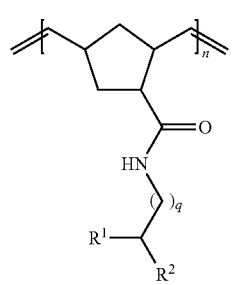
(III)

in which $R^1$ is tri($C_{1-6}$ alkyl)ammonium, with a non-nucleophilic counter-ion, $R^2$ is absent and q is 3.

17. A method for the synthesis of an $^{18}$F-labelled radiotracer, the method comprising:
(i) recovering of $^{18}$F-fluoride ion from $^{18}$O-enriched water containing $^{18}$F-fluoride ion passing the $^{18}$O-enriched water containing $^{18}$F-fluoride ion through a device as claimed in claim 13 or a device comprising two or more devices as claimed in claim 13 which are fluidly interconnected, in which the polymer coating comprises a ROMP polymer of general formula (III):

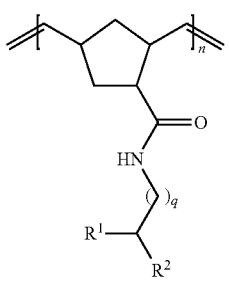
(III)

in which $R^1$ is tri($C_{1-6}$ alkyl)ammonium, with a non-nucleophilic counter-ion, $R^2$ is absent and q is 3; and
(ii) introducing into the device an unlabelled precursor compound of the $^{18}$F-labelled radiotracer such that $^{18}$F becomes incorporated into the precursor compound via nucleophilic substitution to form the $^{18}$F-labelled radiotracer.

18. A method as claimed in claim 17, wherein the $^{18}$F-labelled radiotracer is:

2-[$^{18}$F]fluorodeoxyglucose (2-[$^{18}$F]-FDG);

L-6-[$^{18}$F]fluoro-DOPA;

3'-deoxy-3'-fluorothymidine (FLT);

2-(1,1-dicyanopropen-2-yl)-6-(2-[$^{18}$F]fluoroethyl)-methylamino)-naphthalene ([$^{18}$F]FDDNP);

5[$^{18}$F]fluorouracil; 5[$^{18}$F]fluorocytosine; or

[$^{18}$F]-1-amino-3-fluorocyclobutane-1-carboxylic acid ([$^{18}$F]-FACBC).

* * * * *